(12) United States Patent
Etheredge, III

(10) Patent No.: US 6,689,931 B2
(45) Date of Patent: Feb. 10, 2004

(54) WOUND DRESSING AND METHOD OF MAKING

(75) Inventor: Robert W. Etheredge, III, Natick, MA (US)

(73) Assignee: Tiax LLC, Cambridge, MA (US)

( * ) Notice: Subject to any disclaimer, the term of this patent is extended or adjusted under 35 U.S.C. 154(b) by 315 days.

(21) Appl. No.: 09/879,867

(22) Filed: Jun. 12, 2001

(65) Prior Publication Data

US 2003/0045825 A1 Mar. 6, 2003

(51) Int. Cl.[7] ................................................ A61F 13/00
(52) U.S. Cl. ............................. 602/55; 602/41; 602/42; 602/54
(58) Field of Search .......................... 602/41–59, 900; 428/92, 99, 137, 138, 131, 178–180, 198, 284, 286, 287, 296, 908; 604/304–307, 378, 387, 385.02, 385.03, 391

(56) References Cited

U.S. PATENT DOCUMENTS

| | | | | |
|---|---|---|---|---|
| 3,602,220 A | * | 8/1971 | Bunyan | 128/156 |
| 3,885,559 A | * | 5/1975 | Economou | 128/156 |
| 4,037,601 A | * | 7/1977 | Denkinger | 128/285 |
| 4,147,580 A | * | 4/1979 | Buell | 156/291 |
| 4,207,636 A | * | 6/1980 | Ceriani | 5/481 |
| 4,537,590 A | * | 8/1985 | Pieniak et al. | 604/379 |
| 4,541,426 A | * | 9/1985 | Webster | 128/156 |
| 4,590,113 A | * | 5/1986 | Herzog | 428/92 |
| 4,604,312 A | * | 8/1986 | Creighton et al. | 428/137 |
| 4,699,792 A | * | 10/1987 | Nick et al. | 424/446 |
| 4,725,473 A | * | 2/1988 | Van Gompel et al. | 428/156 |
| 4,773,408 A | * | 9/1988 | Cilento et al. | 128/156 |
| 5,123,900 A | * | 6/1992 | Wick | 602/41 |
| 5,180,620 A | * | 1/1993 | Mende | 428/138 |
| 5,244,457 A | * | 9/1993 | Karami et al. | 602/55 |
| 5,308,313 A | * | 5/1994 | Karami et al. | 602/55 |
| 5,409,472 A | * | 4/1995 | Rawlings et al. | 604/307 |
| 5,681,302 A | * | 10/1997 | Melbye et al. | 604/373 |
| 5,962,112 A | * | 10/1999 | Haynes et al. | 428/198 |
| 6,103,369 A | * | 8/2000 | Lucast et al. | 428/354 |
| 2001/0016245 A1 | * | 8/2001 | Tuman et al. | 428/99 |
| 2001/0018110 A1 | * | 8/2001 | Tuman et al. | 428/99 |

* cited by examiner

Primary Examiner—Kim M. Lewis

(57) ABSTRACT

A wound dressing well suited for mass production on manufacturing assembly lines and having a non-woven fabric reservoir for receiving and retaining wound exudate sandwiched between inner and outer layers of non-woven fabric, the inner layer being adapted for covering a wound, the outer layer being air- and vapor-permeable, but bulk water- and bacteria-impermeable, the inner layer having a plurality of spaced tapering elevations of non-woven fabric, the tapered ends of which are provided with a pressure-sensitive adhesive for adhering the dressing covering a patient's wound.

10 Claims, 1 Drawing Sheet

WOUND DRESSING AND METHOD OF MAKING

By way of illustration, attention is invited to U.S. Pat. No. 4,541,426 issued to Webster, whose discussion of the prior art as background to the invention is additionally worth mentioning.

BACKGROUND OF THE INVENTION

The present invention relates to wound management and, more particularly to novel wound dressings for large scale production and subsequent sale, which invention obviates certain deficiencies to be discussed hereinafter in current industrial protocol for manufacturing dressings for treatment of wounds, burns, incisions and the like.

Irrespective of the dressing design and manner of making, it is most desirable in wound care management to provide a dressing which will maintain the desired moist environment promoting healing while at the same time preventing scab formation; and also permitting removal of wound fluid which can build up a pressure bubble beneath the dressing, thereby undermining the adhesive seal adhering the dressing to the skin and thereby increasing the possibility of the wound being contacted by ambient contaminants, including, of course, microorganisms which can cause infection.

Seemingly, these two objectives are often at cross-purposes so that one of the two objectives is accomplished to the detriment of the other. Yet, dressings alleging to fulfill both objectives have heretofore been described in the patent literature.

As stated in Col. 1 of Webster, it has long been a recognized problem that dressings are inclined to suffer from either or both of the disadvantages that they sometimes tend to float away from a wound or else they sometimes tend adhere to the wound surface.

The former of these disadvantages generally occurs when the wound is one that produces large volumes of exudate. Generally, the method of overcoming this problem is to provide the dressing with holes so that exudate can escape and the dressing remain in contact with the wound. Certain attempts to achieve this end are said to be disclosed in UK Pat. Nos. 778,813; 1,298,011; and 1,408,345; and patent application Ser. Nos. 2,061,732 and 2,074,029. One successful dressing is Melolin™ (Smith & Nephew Ltd.) which comprises a perforated synthetic polymer film and an absorbent cellulosic pad. The perforated film is placed next to the exuding wound so that exudate can pass through the perforations to the overlying absorbent pad where it is absorbed. A later suggestion has been to use a perforated polytetrafluoroethylene film in an effort to minimize the adherence of the dressing to the wound.

Alternatively, dressings have been suggested which comprise a thin hydrophobic film laminated to a fibrous absorbent layer. The film contains a number of apertures in the form of slits. Such dressings are described, for example, in British Pat. Nos. 815,121 and 1,163,452 and U.S. Pat. No. 3,602,220. However, dressings of that type have not been found to be satisfactory because either the slits do not open or they do not open wide enough to allow passage of exudate through the film to the absorbent.

The second of the aforementioned disadvantages generally occurs when the wound has dried out due to lack of production of exudate to maintain a moist environment. Generally, the method of overcoming this problem is to provide the dressing with a continuous layer which retards the rate of loss of water. One effective method of achieving this end is described in British Pat. No. 1,280,631.

The Webster patent then states that none of the known methods are free of disadvantages, since what may be an excellent dressing for one kind of wound will be unsuitable for many other wounds, since wounds differ greatly in their output of exudate. Accordingly, says the patentee, it has now been realized that, not only is there a need for a dressing that is more suitable for use on a number of different types of wounds, there is also a need for a dressing which can better cope with the variation in rate of exudate production from the wound, According to the Webster invention, a dressing has now been discovered which allows passage of a greater amount of exudate from a wound producing larger amounts of exudate, but which allows the wound to remain moist when it produces only smaller amounts of exudate, so that the dressing does not float away from an overly moist surface, nor does it have a tendency to adhere to a dry wound. The new dressing is also said to aid in the re-epithelialisation of the wound.

Accordingly, the patented invention is said to provide a dressing comprising a conformable film with apertures therethrough characterized in that the film comprises a first layer laminated to a second layer, the first layer comprising a material which swells when in contact with water and the second layer comprising a material which when in contact with water does not swell or swells less than the first layer. The apertures are enlarged when in use on a wet surface and otherwise not enlarged, the enlarged openings permitting the passage of water, e.g., wound exudate, the apertures when not enlarged preventing the wound from drying out, i.e., providing a moist environment.

U.S. Pat. No. 5,106,362 issued to Gilman in 1992 discloses a dressing comprising a base sheet for contacting the skin, the base sheet having an opening for placement over the wound and adhesive means for securing the base sheet to the skin; and vent means for providing controlled leakage of fluid along a path from the wound through the opening in the base sheet, the vent means comprising a cover means covering the opening, the cover means permitting the passage of the wound fluid therethrough while reducing evaporation through the opening and thereby helping to insure a moist environment while wound fluid is removed from the wound.

More recently, U.S. Pat. No. 5,308,313 issued to Karami et al. discloses a wound dressing comprising a thin conformable sheet material, a portion of which is adapted for placement over a wound and skin surrounding the wound, the surface of the sheet material adjacent the wound carrying a discontinuous layer of a pressure-sensitive adhesive, the discontinuous layer of adhesive having repeating areas containing no adhesive, at least a portion of only the repeating areas of the sheet material having no adhesive having slits extending through the opposed surfaces to permit transfer of wound fluid unimpeded by presence of adhesive material which can clog the slits, the dressing having an absorbing fabric disposed over the surface of the sheet material opposed from the surface containing the adhesive to provide a reservoir for receiving and retaining wound fluid diffusing to it through the slits; and a cover sheet over the absorbent layer, the cover sheet being air-permeable so that the wound can "breathe", but being bacteria- and water-impermeable.

As will be discussed in detail hereinafter, the present invention is directed to a wound dressing consisting essentially of three layers of non-woven fabrics laid down sequentially to form the dressing. Accordingly, it is thought relevant to acknowledge in the discussion of the BACKGROUND OF THE INVENTION that the concept of providing a wound dressing comprising non-woven fibers is of course known in the art and, further, to mention illustrative patents describing non-woven material useful for this purpose.

U.S. Pat. No. 4,530,353 and a division thereof, U.S. Pat. No. 4,607,633 issued to Lauritzen are directed to the concept of providing low cost wound dressings of the so-called "strip" and "island" adhesive bandage varieties. In Col. 2 of the '353 earlier patent, it is mentioned that the bandages are conveniently prepared from a continuous web having a width equal to the overall length of the desired bandage plus twice the pad length to allow for the Z-fold construction of the patent. In Col. 3 it is stated that the bandage material contemplated by the patentee comprises a mixture of cellulose or other absorbent fibers and polyethylene or other heat-fusible fibers. The heat-fusible fibers are interspersed throughout the web and are preferably present in an amount of at least 10% by weight.

In Col. 4, examples of absorbent fibers to be employed in the practice of the invention include rayon staple fibers, cotton fibers, short length natural cellulosic fibers such as wood pulp fibers and cotton lintners, and mixtures thereof.

The non-woven fabrics described in the Lauritzen patents are further illustrative of the non-wovens that may be employed in the present invention.

The patents mentioned above represent but a cursory search of the art and accordingly are not intended to be indicative of the full state of the patent literature on the recited art. Nevertheless, they are believed to be fairly representative of the prior art to the present invention.

Suffice it to say that nothing in the aforementioned patent literature fully meets the criteria for a non-woven dressing capable of removing excess wound exudate from contact with the wound in a sterile atmosphere through a porous and patterned skin contact layer designed to materially reduce if not to prevent completely skin damage inherent in removal of the dressing, e.g. for replacement of the dressing and/or for inspection of the wound.

It is to this task to which the present invention is directed.

BRIEF DESCRIPTION OF THE INVENTION

In accordance with the present invention, this task is solved in an elegant and cost-effective manner well suited for mass production on manufacturing assembly lines by providing a non-woven wound dressing comprising a non-woven fabric reservoir for receiving and retaining wound exudate sandwiched between what may be described as inner and outer layers of non-woven fabrics, the inner layer being adapted for placement to cover the wound, the outer layer providing an air- and vapor-permeable, but a bulk water- and bacteria-impermeable barrier for the dressing The inner layer has a plurality of spaced tapering elevations of the fabric or "dimples", the tapered ends of which are provided with a pressure-sensitive adhesive. These relatively small spaced deposits together define a discontinuous adhesive layer for adhering the dressing covering the wound.

For a detailed description of the invention and the advantages and improvements over the state of the art it provides, attention is invited to the following detailed description taken in conjunction with the accompanying drawing.

DETAILED DESCRIPTION OF THE INVENTION

Figure 1:
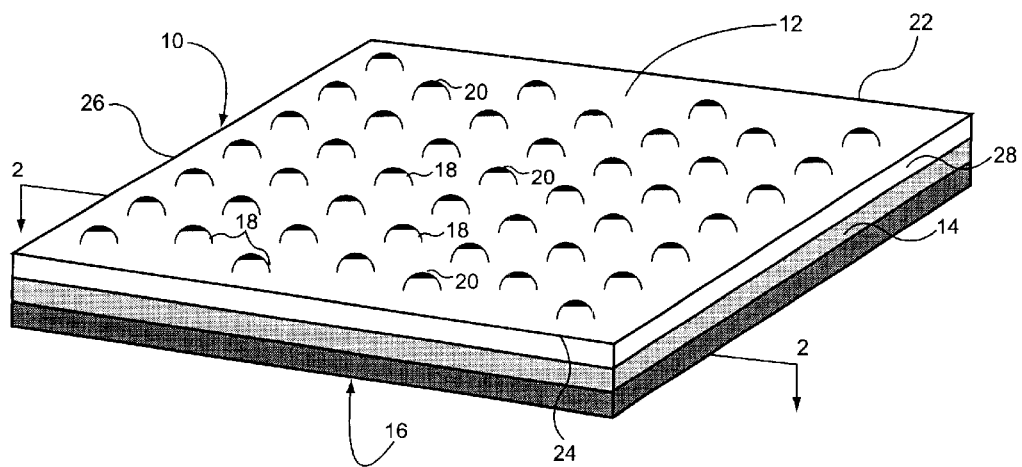
FIG. 1 is a perspective view illustrating one form of a wound dressing of this invention.

As previously mentioned, the present invention is directed to wound care management. More specifically, it is directed to a wound dressing which will provide for wound exudate removal from the surface of the wound so as to minimize the need for dressing changes, while at the same time maintaining the moist environment over the wound which promotes healing while at the same time preventing eschar formation. A most important feature is that the dressing of this invention can be commercially manufactured in an extremely cost-effective manner, as will be discussed hereinafter.

The invention may best be understood by reference to the drawing taken in conjunction with the following detailed description.

Figure 2:
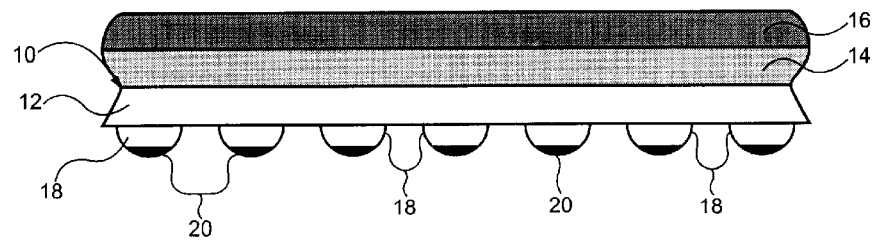
FIG. 2 is a diagrammatic, fragmentary, sectional view, broken away at the edges, of the wound dressing of FIG. 1.

With reference to FIG. 2, the wound dressing (10) is shown to comprise, in order, three layers (12), (14) and (16), respectively, all of non-woven fibers, a portion of which fibers are overlapping and entangled at their respective interfaces to facilitate forming a composite dressing in which the respective layers are retained in superposition to insure the integrity and dimensional stability of the dressing.

The particular shape or configuration of the dressing is immaterial. It may, for example be generally rectangular, circular, or ovate. For purpose of illustration it is shown in the accompanying drawings as being rectangular, having end edges (22) and (24) connecting side edges (26) and (28) to form a rectangular configuration.

Layer (12), which for simplicity will hereinafter be referred to as the "inner layer", is to be applied directly over the wound. To allow this layer to flex with the skin surface and to reduce the incidence of shear failure within the skin, the non-woven fibers may comprise a substantial amount of elastic or viscoelastic fibers. Layer (12) may also be made of "wettable" but non-absorbent fiber facilitating diffusion or wicking of wound exudate thorough the interstices of the fibers and then to the overlying layer. Alternatively, layer 12 may comprise a mixture of both elastic or viscoelastic fibers and wettable non-absorbent fibers, as previously discussed.

Further, the non-woven fabric (12) should preferably be of a material that does not permit insult to the healing wound by allowing bandage particles to come free and enter the healing wound. Layer (12) preferably should also prevent any abrasion or irritation to the wound from the overlying layer (14).

Useful non-woven fibers for layer (12) are per se known in the art and their selection will be a matter of choice within the expected judgment of the skilled worker in the light of this description. Nevertheless, for purposes of illustration, mention may be made of non-wovens containing apertures such as "KEYBACK" (trademark of Chicopee Mfg. Co., or "SPUNLACE" (trademark of Burlington Industries), etc., as well as non-wovens such as spunbond materials.

In any case, layer (12) may, for example, be on the order of from about 0.05 to about 1.00 mm thick and may range from about 10 to about 30 grams/yard$^2$ by weight.

A very important, in fact a critical aspect of the present invention is that layer (12) is provided with a paternwise distribution of small elevated hemispheres or "dimples"

(18), the tips of which contain a small amount of pressure-sensitive adhesive (20), e.g. any of the medical grade or hypoallergenic pressure-sensitive adhesives heretofore employed for applying bandages, gauze and the like to the skin. Such per se known adhesives include rubber-based, acrylic, vinyl ether and silicone pressure-sensitive adhesives. In lieu of pressure-sensitive adhesives, water- or heat-activated adhesives are also within the scope of this invention. In any case, the selected adhesive will be a matter of individual choice within the expected knowledge of the practitioner of this invention and accordingly will not per se comprise any part of this invention.

The inner layer (12) may be formed by deposition from melt-blown, spunbond or other non-woven material against a porous platen having a topography designed to produce the desired spaced elevations (18).

The amount of such deposits that will be required to satisfactorily retain the dressing on the skin will in part be dependent upon the aggressiveness of the adhesive selected as well as the concentration of the adhesive deposits. For this reason there is no proper way to quantify precisely the required concentration of the adhesive deposits (20) on layer (12). This can only be done as appears herein and in the appended claims by a "functional" description, i.e., in "an amount sufficient to retain the dressing on the skin."

By way of illustration, however, these individual hemispheres of adhesive (20) may be on the order of about 1.0 to about 2.0 mm in diameter at their tip, from about 0.5 to about 1.0 high, and they may be deposited in a hexagonal array spaced on the order of about 2.0 mm from one another to provide on the order of at most 45% coverage of the total area of the individual hemispheres (18).

The adhesive deposits (20) will preferably be applied after completing formation of the tri-layer configuration of the dressing of this invention. A particularly useful way of doing this is by means of a hot melt applicator, or, alternatively by transfer coat lamination from adhesive on a release liner.

Layer (14), which Applicant thinks of as being a reservoir for receiving and retaining wound exudate diffusing through the interstices of the underlying layer (12) may comprise any of the highly absorptive non-woven fibrous materials heretofore employed in wound dressings to absorb and retain exudate, e.g., gauze sponges, absorbent pads such as those customarily employed in finger bandages or, for larger dressings, used for abdominal surgery, and the like. Preferably, it will comprise, a heat-bondable, absorbent, non-woven fabric which is characterized as providing loft and absorbency. It is preferably composed of absorbent fibers such as cellulose or rayon and heat-fusible fibers such as polyethylene and polypropylene in such relative proportions that the absorbent layer is subjectively described as being both soft and highly absorbent, as well as being strong and dimensionally stable. The heat-fusible fibers are interdispersed throughout the fabric and may for example consist of at least 10% by weight of the total weight of non-woven material in layer (14). Layer (14), which may for example be on the order of 1.0–3.0 mils thick, may additionally contain other materials performing specific desired functions, e.g. an antimicrobial agent such as chlorhexidine, although the use of such reagents is not thought necessary.

It is pointed out that the broad general concept of employing a discontinuous adhesive layer consisting of a patternwise deposition of individual adhesive deposits in order to retain a dressing adhered to the skin is not per se new. It is described and claimed in the aforementioned U.S. Pat. No. 5,308,313 issued to Karami et al.

However, it is believed to be both novel and inventive to provide the discontinuous layer in the manner described above. This is an important feature of this invention.

While the prior patternwise adhesive deposits are applied to a generally planar layer surface, according to the present invention the adhesive deposits are applied to the elevations (18) defined previously as "dimples" or "hemispheres" rising over the planar surface of layer (12)

Conventional adhesives cold flow, especially under conditions of pressure and elevated temperature inherent in storage of the dressings. The benefit of providing adhesive dots as contemplated by the present invention would be lost once they flow and coalesce. However, the non-woven topography of the present invention provides a stable foundation upon which to coat the adhesive and thereby tends to impart permanence to the discontinuous coating.

Thus, attachment to the skin will be accomplished with less adhesive as well as with less removal damage to the skin in accordance with the present invention in which the individual adhesive deposits are elevated on layer (12) as deposits on the dimples or hemispheric elevations (18) of layer (12).

The outer layer (16) is applied immediately after forming the reservoir middle layer (14). As heretofore mentioned, layer (16), which is designed to prevent contamination of the dressing and the underlying wound from environmental contaminants, is characterized as being air-permeable, but as being both water- and bacteria-impermeable. It may, for instance, comprise a non-woven spunbond polyolefin such as "TYVEK"® or equivalent which provides a waterproof but porous network to resist bulk water absorption yet allow transpiration of water vapor. Layer 16 may be on the order of from about 1.0 to about 3.0 mils thick. While not necessary, it may optionally contain a per se known bacterial barrier air filter such as "NUCLEOPOREF"®, "MILLIPORE"® or "GELLMAN"®, etc. The novel dressing of this invention affords certain advantages over the prior art.

It does not require a pad, as such, since the second layer absorbs exudate over the entire area. Since the discontinuous adhesive layer covers the full area of the dressing, there is no need to zone coat the dressing to keep adhesive from wound contact. Wound fluid contacts the hypoallergenic adhesive of conventional bandages as well. Moreover, adsorbed proteins, lipids, and other exudate products tend to deaden the adhesive over the wound bed. Further, use of a hypoallergenic adhesive will ensure that no deleterious reagents are discharged into the wound bed. The dressings can be made single width or wider in fewer passes than the prior art ones. They may be thermally slit to bond the edges to prevent tearing, fraying, etc., and to strengthen the dressing.

The present invention provides certain very significant improvements in the wound care art, as will be described hereinafter.

Initially, it is to be noted that the patternwise deposition of adhesive necessary to adhere the dressing to cover the wound is provided by depositing adhesive tips 20 to the elevated dimples 18 on inner layer 12. This is readily distinguishable from the patternwise distributions of adhesive on the planar surface of an elastomer sheet material, as taught by the aforementioned U.S. Pat. No. 5,308,313, the adhesive-free areas of the elastomeric sheet material then be provided with slits to permit wicking of wound exudate to an overlying absorbent layer.

This novel feature of the present invention utilizes less adhesive than the dressing in the aforementioned '313 patent, a significant cost-saving in manufacture and the inner layer 12 of the present invention is substantially more "wound-friendly", causing much less damage to the wound and, additionally to the skin surrounding the wound, on removal.

Further, it will be appreciated that the non-woven layer 12 inherently permits more efficient and rapid wicking of wound exudate away from the wound to the overlying reservoir layer 14 which, as pointed out in the '313 patent can build up to a pressure bubble beneath the dressing, thereby undermining the adhesive seal to the skin and thus increase the possibility of the wound being subjected to ambient contaminants, including microorganisms which can cause infection. Because of the improved efficiency of wound exudate removal the present invention provides, it will be appreciated that the number of times a dressing need be replaced can be significantly minimized and this, in turn, reduces the likelihood of damage to the wound resulting from the removal(s).

Next, as was mentioned above, the patternwise adhesive deposition of the Karami et al. system recited in U.S. Pat. No. 5,308,313 relies upon slits in the non-adhesive areas to permit wicking of wound exudate through the elastomeric sheet material carrying the adhesive deposits, the present invention utilizes non-woven fibers in the inner layer as well as the other layers of the dressing. Since the non-woven fibers provide a highly permeable layer, wicking of wound exudate in the dressing of this invention is appreciably more rapid and efficient than that provided by slitting in the prior art dressing.

Continuing, since the three layers comprising the present invention are all made from non-woven fabrics, the laying down of the successive layers will inherently cause interlinking or interlocking at least at the interface between adjacent layers, thereby providing excellent structural integrity to the dressing.

Further, the non-woven material of layer 12 is very compliant and thereby provides high flexibility of the dressing to the skin of the patient.

Finally, the inner layer can be configured without heat which can contribute to degradation in manufacture.

The foregoing discussion of advantages of the present invention which taken alone or in combination can be considered to constitute patentable novelty, the following additional advantages are also meritorious enough to warrant comment.

Useful in both acute and chronic embodiments;

Attractive to major practitioners in both;

Alternative dressings are too expensive to produce for mass use;

Simplified converting in assembly;

Consumer acceptance;

Short path for regulatory clearance for manufacture and sale;

Small area of adhesive contact reduces damage to wound during removal;

At least 50% reduction in quantity of adhesive required;

Dressing flexes with skin during activity;

Absorptive central layer removes exudate over the full dressing area;

Manufacture requires fewer steps and smaller manufacturing space;

Dressing can be thermally slit to bond periphery and eliminate tearing;

Design will support new drug delivery designs; and

Overall cost of manufacture should be much lower.

Since certain changes may be made without departing from the scope of the invention, it is intended that the foregoing detailed description along with the accompanying drawing should be taken as being illustrative only and not in a limiting sense.

What is claimed is:

1. A wound dressing comprising an intermediate reservoir layer adopted for receiving and retaining wound exudate sandwiched between an inner layer adapted for placement covering a wound and an outer layer providing a cover for the dressing, each of the reservoir, inner and outer layers consisting essentially of non-woven fibers at least a portion of which are overlapping and entangled at the layers' respective interfaces, whereby the respective layers are retained in superposition by the overlapping and entangled fibers to insure integrity and dimensional stability of the wound dressing;

the inner layer being characterized by a generally planar surface having a plurality of spaced elevations of the non-woven fibers extending above the planar surface of non-woven fibers;

the spaced elevations of non-woven fibers having an adhesive coating on their tips, the number of adhesive-coated spaced elevations and the amount and aggressiveness of the adhesive together constituting an amount of adhesive sufficient to retain the dressing in placement when positioned on a patient's skin to cover a wound;

the intermediate reservoir layer being characterized as consisting of highly absorbent non-woven fibers adopted for receiving and retaining wound exudate wicking through the non-adhesive-containing planar surface of the inner layer to the reservoir layer; and the outer layer being adapted for preventing contamination of the dressing and the underlying wound from environmental contaminants, the outer layer being characterized as being air- and vapor-permeable but as being a bacteria- and bulk water-barrier to transmission therethrough.

2. A wound dressing as defined in claim 1 wherein the spaced elevations are in a patternwise deposition covering substantially the entire area of the inner layer.

3. A wound dressing as defined in claim 2 wherein each of the spaced elevations is tapered in the form of a dimple.

4. A wound dressing as defined in claim 1 wherein the non-woven fibers in the inner layer include non-woven elastic or viscoelastic fibers in an amount sufficient to allow the inner layer contacting a patient's skin to flex with the skin surface and thereby to reduce the incidence of shear failure with the skin.

5. A wound dressing as defined in claim 1 wherein each of the spaced elevations consists essentially of non-woven fibers from the planar surface of the inner layer having an end portion tapering from the planar surface of the inner layer towards the elevation's tip to provide a pattern of tapering spaced elevations covering substantially the entire area of the inner layer, each tapered elevation having a small quantity of pressure-sensitive adhesive coated on its tapered end portion for engaging a patient's skin when the dressing is applied.

6. A wound dressing as defined in claim 5 wherein the elevations are in the general form of a dimple deposited in a geometric pattern with the adhesive on each dimple being on the order of about 1.0 to about 2.0 mm in diameter at its tip and being from about 0.5 to about 1.0 mm in length.

7. A wound dressing as defined in claim 1 wherein the non-woven reservoir layer comprises a mixture of highly absorbent fibers and heat-fusible fibers in such relative proportions that the reservoir layer is characterized as being both soft and highly absorbent, as well as being strong and dimensionally stable.

8. A wound dressing as defined in claim 7 wherein the heat-fusible fibers comprise at least 10% by weight of the total weight of non-woven fibers in the reservoir layer.

9. A method for forming a wound dressing comprising the steps of (1) forming a first layer of non-woven fibers by deposition of the fibers against a porous platen having a topography designed to produce a pattern of spaced elevations of the non-woven fibers extending from a generally planar surface of the layer, the spaced elevations tapering from the planar surface of the layer to an end portion;

(2) forming a second layer of non-woven fibers on the surface of the first layer opposed from the surface of the first layer having the spaced elevations, the second layer being characterized as being highly absorptive of wound exudate, at least a portion of the fibers of the first and second layers overlapping and being entangled at the interface between the respective layers;

(3) forming a third layer of non-woven fibers over the free surface of the second layer, the third layer being characterized as being air- and vapor-permeable, but as being bulk water- and bacteria-impermeable, at least a portion of the fibers of the second and third layers overlapping and being entangled at the interface between the second and third layers;

(4) removing the composite structure consisting of the three layers of non-woven fibers from the platen; and (5) applying a coating of a pressure-sensitive adhesive on the end portion of substantially all of the tapered elevations.

10. A method as defined in claim 9 wherein the third layer is formed immediately after forming the second layer in order to prevent contact of the wound or underlying layers of the wound dressing with environmental contaminants.

* * * * *